United States Patent [19]
Fujimoto et al.

[11] 3,937,802
[45] Feb. 10, 1976

[54] SPRAYABLE HAIR-SETTING COMPOSITION CONTAINING A SULFONATE CONTAINING HYDROPHILIC COPOLYMER

[75] Inventors: Takehiko Fujimoto, Habayoshi; Tetsuo Kakehi, Kyoto; Kazumichi Susaki, Gojobashi-higashi, all of Japan

[73] Assignee: Sanyo Chemical Industries, Ltd., Kyoto, Japan

[22] Filed: Aug. 23, 1973

[21] Appl. No.: 390,848

[30] Foreign Application Priority Data
Aug. 24, 1972  Japan.............................. 47-84854

[52] U.S. Cl. .................... 424/47; 8/10.1; 8/127.51; 260/296 R; 260/328 R; 260/33.8 H; 260/78.3 M; 424/DIG. 1; 424/DIG. 2; 424/DIG. 3; 424/DIG. 5; 424/61; 424/62; 424/64; 424/70; 424/71; 424/78; 424/81
[51] Int. Cl.² ........................................... A61K 7/11
[58] Field of Search .... 260/79.3 M, 29.6 R, 32.8 R, 260/33.8 UA; 424/47, 71, 81, 78, 70, DIG. 1, DIG. 2

[56] References Cited
UNITED STATES PATENTS

| | | | |
|---|---|---|---|
| 2,531,468 | 11/1950 | Reynolds et al................ | 260/79.3 M |
| 2,604,461 | 7/1952 | Roth............................... | 260/79.3 M |
| 2,837,500 | 6/1958 | Andres et al................... | 260/79.3 M |
| 3,008,918 | 11/1961 | Stanton et al...................... | 260/45.5 |
| 3,257,281 | 6/1966 | Maeder................................. | 424/47 |
| 3,320,212 | 5/1967 | Shen et al.......................... | 424/78 X |
| 3,576,760 | 4/1971 | Gould et al........................ | 424/81 X |
| 3,577,518 | 5/1971 | Shepherd et al...................... | 424/47 |
| 3,644,303 | 2/1972 | Berger et al. ...................... | 424/81 X |
| 3,671,502 | 6/1972 | Samour et al.................. | 260/79.3 M |
| 3,706,717 | 12/1972 | Siegele........................... | 260/78.5 R |

*Primary Examiner*—Albert T. Meyers
*Assistant Examiner*—Vera C. Clarke
*Attorney, Agent, or Firm*—Oblon, Fisher, Spivak, McClelland & Maier

[57] ABSTRACT

A hair-dressing composition for setting and imparting greater luster to hair which comprises, a hydrophilic polymer containing at least 3% by weight structural units which contain at least one sulfonate group.

3 Claims, No Drawings

A SPRAYABLE HAIR-SETTING COMPOSITION CONTAINING A SULFONATE CONTAINING HYDROPHILIC COPOLYMER

BACKGROUND OF THE INVENTION

1. Field of the Invention

This invention relates to cosmetic compositions. More particularly, this invention relates to compositions such as hair lacquers and hair lotions for setting and adding luster to the hair.

2. Description of the Prior Art

Various synthetic resins have been used extensively to prepare hair compositions which add luster to the hair and for setting hair. Examples of these synthetic resins include polyvinylpyrrolidone, vinylpyrrolidone/vinylacetate copolymers, alkyl or alkanol amine salts of acrylic acid ester/monoethylenically unsaturated acid copolymers and alkyl or alkanol amine salts of maleic acid monoester/alkylvinyl ether copolymers. The resins which are used in the hair treating compositions must have a variety of properties such as (1) solubility in water, alcohols or mixtures thereof, (2) good compatibility with other components for cosmetic compositions (especially with propellants when used in the form of an aerosol spray), (3) good hair-setting properties and (4) good adhesion. Furthermore, hair treated with the resins should have (1) high gloss, (2) exhibit no flaking, (3) have no tackiness and exhibit good curl retention at high humidities, and (4) have good washability.

The conventional resins presently in use are satisfactory in some of the properties listed above. However, they also lack some of the other desirable properties. For example, the homopolymer or copolymers of vinylpyrrolidone have good hair-setting properties, but they have the objectionable property of flaking when hair treated with the resins is combed. In addition, treated hair tends to become so soft and tacky in humid atmospheres that individual fibers of the treated hair will adhere to each other, which makes combing or brushing difficult. The salts of acrylic acid ester copolymers impart good adhesion to the hair and do not flake as readily, but they have poor washability properties and poor curl retention properties at high humidities. The salts of maleic acid monoester copolymers exhibit many of the good properties desired for hair treating compositions. However, they have poor compatibility with halogenated hydrocarbons which are used as propellants in aerosol sprays.

A need, therefore, continues to exist for a hair composition whose properties are optimum with regard to all of the properties desired in a hair treating composition.

SUMMARY OF THE INVENTION

Accordingly, one object of this invention is to provide a cosmetic composition having improved properties.

Another object of this invention is to provide a hair dressing composition.

Yet another object of this invention is to provide a hair-setting composition.

Still another object of this invention is to provide a hair spray composition for setting and adding luster to the hair.

Briefly, these objects and other objects of the invention as hereinafter will become more readily apparent can be attained by a cosmetic composition which comprises a hydrophilic polymer containing at least 3 weight % of structural units containing at least one sulfonate group, (hereinafter referred to as the sulfonate-containing unit).

DETAILED DESCRIPTION OF THE PREFERRED EMBODIMENTS

The sulfonate group in the sulfonate-containing unit of the polymer of the invention may be represented by the following formulas:

 (1)

 (2)

wherein M is a metal, $m$ is the valency of M, and M' is ammonia or an organic amine. Suitable examples of M include alkali metals such as Li, Na and K, and alkaline earth metals such as Ca and Mg. Suitable examples of M' are ammonia ($NH_3$), primary amines such as methyl amine, ethyl amine and monoethanol amine, secondary amines such as dimethyl amine, diethyl amine, diethanol amine, methylethanol amine and morpholine, and tertiary amines such as trimethyl amine, triethanol amine and imidazoline derivatives. Preferred examples of M are the alkali metals, while the preferred examples of M' are primary, secondary and tertiary amines containing lower alkyl ($C_1 - C_3$) substituents or hydroxyalkyls ($C_1 - C_3$), and morpholine.

The sulfonate-containing unit of this invention can be represented by the following formula:

$$Z—(X)_n—(\text{sulfonate group}) \quad (3)$$

wherein Z is a trivalent unit which constitutes the main chain of the hydrophilic polymer, X is a divalent linking group, and $n$ is 0 or 1. A more specific representation of formula (3) is:

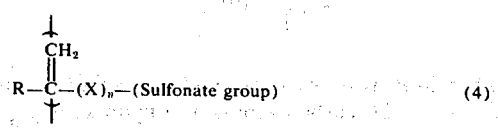 (4)

wherein R is H, a hydrocarbon radical containing from 1 – 4 carbon atoms, or nitrile (—CN), and X and n are the same as shown in formula (3). Suitable examples of group X in formulas (3) and (4) include —A—,

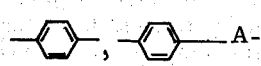

—COOA—, —OOC—A—, —CONH—A— and —COO—(AO)$_p$—A—, wherein A is lower alkylene ($C_1 - C_4$), $p$ is an integer from 1 – 10, and the benzene rings can have at least one substituent.

More specific representations of the structural unit represented by formula (4) are:

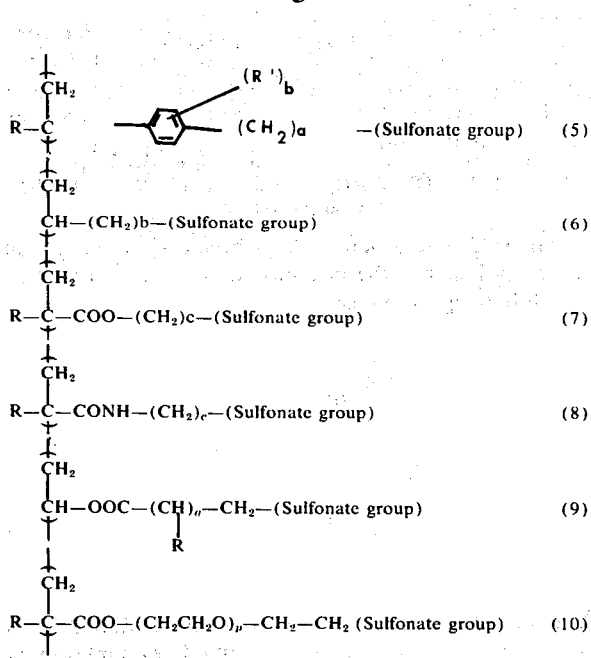

(5) —(Sulfonate group)

$R-CH_2-CH-(CH_2)_b-(Sulfonate\ group)-CH_2$ (6)

$R-C(CH_2)-COO-(CH_2)_c-(Sulfonate\ group)$ (7)

$R-C(CH_2)-CONH-(CH_2)_c-(Sulfonate\ group)$ (8)

$CH-OOC-(CH)_a-CH_2-(Sulfonate\ group)$ with R (9)

$R-C(CH_2)-COO-(CH_2CH_2O)_p-CH_2-CH_2\ (Sulfonate\ group)$ (10)

wherein R is H or methyl, R' is methyl or ethyl, $a$ is 0 or 1, $b$ is an integer from 0 to 4, $c$ is an integer from 1 to 3, and $p$ is an integer from 1 to 10. Among the units represented by the formulas (5) through (10), the most preferred representations are units shown by the formula (7).

The content of the sulfonate-containing unit in the hydrophilic polymer should be at least 3% by weight, when the solubility of the polymer in water or alcohols and other properties of the resulting cosmetic composition are considered. Preferably the content of the sulfonate-containing unit is in the range of 3 – 95% by weight, more preferably 10 – 50% by weight.

The hydrophilic polymer of this invention may also contain at least one other structural unit. Examples of these structural units are units which are derived from comonomers which will be described in the processes for producing the hydrophilic polymer. The preferred structural units can be represented by the formula:

(11)

wherein $R_1$ is H or methyl, and $R_2$ is an alkyl containing from 1 to 20 carbon atoms or a hydroxyalkyl containing from 1 to 4 carbon atoms. Mixtures of the structural units can also be advantageously used.

The hydrophilic polymer of this invention can be produced by any conventional method. Thus, the polymer may be obtained by polymerizing an ethylenically unsaturated monomer containing a sulfonic acid (or its salt) group (hereinafter referred to as the sulfonate-containing monomer), or by copolymerizing the monomer with at least one polymerizable comonomer. If a monomer containing a free sulfonic acid group is used, the free acid group of the resulting polymer is neutralized with a basic compound. Another method of obtaining the hydrophilic polymer comprises producing a homopolymer or a copolymer containing no sulfonate group or sulfonic acid group as an intermediate, and then subjecting the intermediate to sulfonation by treating the polymer with a sulfonating agent such as sulfuric acid, chlorosulfuric acid or a sulfone, followed by neutralization with a basic compound. For example, styrene (or acrylic acid) is polymerized to form polystyrene (or polyacrylic acid) as the intermediate. Thereafter, the polymer is reacted with sulfuric acid (or a sulfone).

Examples of the sulfonate-containing monomer used for the production of the hydrophilic polymer are represented by the following formulas:

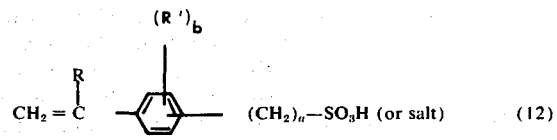

(12)

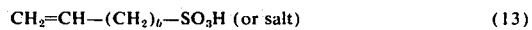

(13)

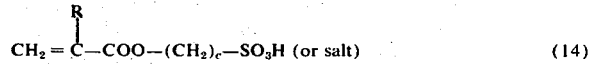

(14)

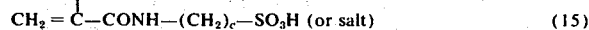

(15)

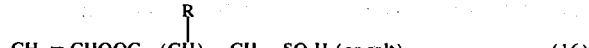

(16)

(17)

wherein R, R', $a$, $b$, $c$ and $p$ are as defined before.

Suitable sulfonate-containing monomers of formulas (12) to (17) include para-and ortho styrene sulfonic acid and 3-vinyltoluene-6-sulfonic acid, formula (12); ethylene sulfonic acid and 1-propene-3-sulfonic acid, formula (13); sulfomethyl acrylate, 2-sulfoethyl acrylate, 3-sulfopropyl acrylate, and methacrylates corresponding thereto, formula (14); N-acryloyl taurine and N-methacryloyl taurine, formula (15); vinyl sulfoacetate and vinylsulfopropionate, formula (16); sulfoethyloxyethyl acrylate, sulfoethylpoly (oxyethylene) acrylates and methacrylates corresponding thereto, formula (17); and salts thereof. Mixtures of these monomers may also be used.

A comonomer(s) can be reacted with the sulfonate-containing monomer. Suitable comonomers used with the sulfonate-containing momoner include aliphatic acid esters of unsaturated alcohols such as vinyl acetate, vinyl propionate, allyl acetate, allyl propionate, and the like; aliphatic vinyl ethers such as methyl vinyl ether, ethyl vinyl ether, lauryl vinyl ether, and the like; styrene compounds such as styrene, vinyltoluene, vinyl naphthalene, and the like; alkyl acrylates such as methyl acrylate, ethyl acrylate, 2-ethylhexyl acrylate, lauryl acrylate, oleyl acrylate, and the like; alkyl methacrylates corresponding to the above acrylates; hydroxyalkyl acrylates such as hydroxymethyl acrylate, hydroxethyl acrylate, hydroxypropyl acrylate, and the like; hydroxyalkyl methacrylates corresponding to the above acrylates; alkylene ($C_1$–$C_4$) oxide adducts of acrylic acid or methacrylic acid; acrylamides; methacrylamides and acrylonitrile. Of these comonomers, the preferred ones are alkyl $(C_1-C_{20})$ acrylates, alkyl $(C_1-C_{20})$ methacrylates, hydroxyalkyl $(C_1-C_4)$ acrylates and hydroxyalkyl $(C_1-C_4)$ methacrylates. Mixtures of these comonomers may also be used.

When the sulfonic groups in the resulting polymer are free acid groups, they are neutralized with a basic compound. Suitable basic compounds include alkali metal hydroxides such as lithium, potassium, sodium hydroxides, and the like; ammonia; alkyl amines such as monomethyl amine, dimethyl amine, trimethyl amine, monoethyl amine, diethyl amine, triethyl amine, and the like; aminoalcohols such as mono- di- and triethanol amines, mono-, di- and tripropanol amines, aminoethyl ethanol amine, aminomethyl propanol amine, aminomethyl propanediol, and the like and morpholine.

The polymerization reaction of this invention can be conducted by any suitable procedure such as solution or suspension polymerization. Preferably, the reactions are conducted by a solution polymerization procedure in the presence of a solvent and a catalyst at the reflux temperature of the solvent. Suitable solvents include aliphatic alcohols containing from 1 to 4 carbon atoms, dioxane, methyl ethyl ketone, acetone, tetrahydrofuran, methyl Cellosolve, ethyl Cellosolve, and mixtures thereof. A mixture of any of the solvents with a small quantity of water (e.g., 95% by volume alcohol solution) can also be used. Suitable catalysts include peroxides such as benzoyl peroxide, acetyl peroxide, lauroyl peroxide, and the like and azo compounds such as $\alpha, \alpha'$ - azobisisobutyronitrile, azobisdimethyl valeronitrile, and the like. All the other reactions such as sulfonation and neutralization reactions which are used throughout the process of this invention are well known procedures.

The hydrophilic polymer of this invention can be used in various kinds of hair dressing compositions such as hair sprays for setting hair, hair setting lotions, other hair lotions, hair liquids, hair conditioners, hair tonics, hair coloring preparations and hair bleaching preparations. The polymer is particularly useful in hair dressing compositions for use in setting hair or adding luster to the hair.

The hair dressing composition of this invention comprises the hydrophilic polymer and one or more components which are used in conventional hair dressing compositions. The composition can be prepared by incorporating the hydrophilic polymer as an additive into a conventional hair dressing composition or it can be used in the composition in place of one or more conventional components. The amount of the polymer used in the hair dressing composition may vary over a wide range according to the kind of hair dressing composition desired. Generally, from 0.1 to 20% by weight, preferably from 0.5 to 10% by weight of the polymer is used based on the total weight of the composition. Suitable conventional components which may be used in the hair dressing composition of this invention are solvents such as water, ethanol, ethylene glycol, propylene glycol, glycerine, ethyleneglycol monoethyl ether, and the like; mineral oils, vegetables oils, waxes, polyoxyalkylene ethers, resins such as polyvinyl pyrrolidone, or the like; lanolin, lanolin derivatives, perfumes, dyes, pigments, softening agents, emollients, lustering agents, stimulants, antiseptics, lubricants, penetrants, plasticizers and diluents.

Optimum use of the hydrophilic polymer of this invention is achieved when the polymer is used to prepare compositions which add luster to the hair and set the hair such as aerosol sprays and hair-setting lotions. These compositions can be prepared from the polymer in the same manner conventional compositions are prepared from conventional resins. For example, a hair spray can be prepared by dissolving the hydrophilic polymer in a solvent, and then placing the resulting solution with a propellant in a suitable pressure container fitted with a spray nozzle. A hair-setting lotion can be prepared by just mixing the polymer and a solvent.

Suitable solvents for use in the spray and lotion composition include water, $(C_1-C_4)$ aliphatic alcohol dioxane, methyl ethyl ketone, acetone, tetrahydrofuran, methyl Cellosolve, (ethylene glycol monomethyl ether) ethyl Cellosolve, (ethylene glycol monoethyl ether) and mixtures thereof. The preferred solvents include water, ethanol, and water-ethanol mixtures for the lotions and ethanol for the sprays. Suitable propellants for the sprays include halogenated hydrocarbons such as trichloromonofluoromethane, dichlorodifluoromethane, dichlorotetrafluoroethane, and the like, liquified petroleum gases such as propane, butane, and the like and mixtures thereof.

The amounts of the hydrophilic polymer, the solvent and the propellant used for the formulation of the sprays encompass the ranges listed below.

| | |
|---|---|
| Polymer | 0.5 – 5 wt % (preferably 1 – 3 % by weight) |
| Solvent | 20 – 65 wt % (preferably 25 – 50 % by weight) |
| Propellant | 30 – 79.5 wt% (preferably 47 – 72 % by weight) |

The amounts of the hydrophilic polymer and the solvent used for the formulation of the lotions encompass the ranges listed below.

| | |
|---|---|
| Polymer | 1 – 10 wt % (preferably 3 – 8% by weight) |
| Solvent | 90 – 99 wt % (preferably 92 – 97% by weight) |

Optional additives may be incorporated into the hair sprays and lotion formulations. These additives include plasticizers such as glycerine, ethylene glycol, sorbitol, polyethylene glycol, and dialkylphthalates such as dimethylphthalate, dibutylphthalate, and the like; and lanolin, dyes, perfumes, and other hair dressing components inclusive of the ones listed earlier.

When the hydrophilic polymer is used to prepare shampoos and hair rinses, it is used in amounts of 2–4 weight % based on the total weight of the composition.

It has also been found that the hydrophilic polymer can be advantageously used in other cosmetic compositions other than hair dressing compositions. These cosmetic compositions are cosmetics which have been used to cover human skin or finger to toe nails with a thin film of material. The cosmetics include lipsticks, nail lacquers and various creams and lotions. The amount of the polymer used in the cosmetic composition generally ranges from 0.5 to 5 percent by weight of the total weight of the cosmetic composition.

The hair and cosmetic compositions formulated with the polymer of this invention have several advantages. Thus, in the case of hair dressing compositions, the compositions have (1) good hair-setting properties, (2) good stability (because the hydrophilic polymer has good compatibility with other components), and (3)

good removability when the hair is washed (because the hydrophilic polymer is soluble in water). Furthermore, hair treated with the composition has (1) good gloss, (2) exhibits no flaking (because the hydrophilic polymer has good adhesion to the hair fibers), and (3) exhibits no tackiness and has good curl retention even at high humidities. When the polymer is used in shampoos and hair rinses, hair treated with compositions containing the polymer have good gloss. Lipsticks and finger nail lacquers which contain the polymer of the invention in the cosmetic compositions exhibit good adhesion to the skin or nails as well as having good film-forming properties.

Having generally described this invention, a further understanding can be obtained by reference to certain specific examples which are provided herein for purposes of illustration only and are not intended to be limiting unless otherwise specified.

EXAMPLE 1

Into a four-necked, round-bottomed flask equipped with a thermometer, a reflux condenser, a dropping funnel and an agitator, was charged 140g of sulfopropyl methacrylate, 200g of ethyl methacrylate, 170g of hydroxethyl methacrylate, 430g of ethyl acrylate, 700g of ethyl alcohol and 5g of azobisdimethylvaleronitrile. The stirred mixture was heated at reflux (about 79°–81°C.) under a nitrogen atmosphere for 6 hours. A copolymer solution in ethyl alcohol was obtained with a polymerization degree of over 99 percent. To the stirred copolymer solution was added dropwise an alkaline solution which was obtained by dissolving 26g of caustic soda in a mixture of a small amount of water and 300g of ethanol. By this procedure was obtained about 50% by weight of a solution containing a neutralized copolymer whereby the solution had a viscosity of about 40,000 cps. at 25°C.

EXAMPLE 2

Into the same flask used in Example 1, was charged 140g of sodium sulfopropyl methacrylate, 380g of ethyl methacrylate, 160g of hydroxyethyl methacrylate, 320g of ethyl acrylate and 900g of a 95% by volume aqueous solution of ethanol. The stirred mixture was refluxed at 79°–81°C under a nitrogen atmosphere for 6 hours, while a solution was added dropwise thereto which was obtained by dissolving 5g of azobisdimethyl-valeronitrile in 100g of a 95% by volume aqueous solution of ethanol. By this procedure there was obtained about a 50% by weight solution of a copolymer which solution had a viscosity of about 45,000 cps at 25°C and a polymerization degree greater than 99 percent.

EXAMPLE 3

Example 2 was repeated wherein 140g of sodium sulfoethyl methacrylate, 350g of ethyl methacrylate, 170g of hydroxethyl methacrylate, 340g of ethyl acrylate and 900g of a 95% by volume aqueous solution of ethanol was used. By this procedure was obtained a 50% by weight solution of a copolymer which solution had a viscosity of about 43,000 cps at 25°C.

EXAMPLE 4

Example 2 was repeated wherein 140g of sodium styrene sulfonate, 300g of ethyl methacrylate, 140g of hydroxyethylmethacrylate, 420g of ethylacrylate and 900g of a 95% by volume aqueous solution of ethanol was used. By this procedure was obtained a 48% by weight solution of a copolymer which solution had a viscosity of about 37,000 cps at 25°C.

EXAMPLE 5

Example 2 was repeated wherein 140g of sodium ethylene sulfonate, 380g of ethylmethacrylate 140g of hydroxyethyl methacrylate, 340g of 3-methoxybutyl methacrylate and 900g of a 95% by volume aqueous solution of ethanol was used. By this procedure was obtained a 48% by weight solution of a copolymer which solution had a viscosity of about 35,000 cps at 25°C.

EXAMPLE 6

Example 2 was repeated wherein 140g of sodium N-acryloyl taurine, 360g of ethylmethacrylate, 140g of hydroxyethyl methacrylate, 360g of ethyl acrylate and 900g of a 95% by volume aqueous solution of ethanol was used. By this procedure was obtained a 50% by weight solution of a copolymer which solution had a viscosity of about 47,000 cps at 25°C.

EXAMPLE 7

Example 2 was repeated wherein 140g of sodium vinyl sulfoacetate, 350g of ethylmethacrylate, 140g of hydroxyethyl methacrylate, 370g of ethylacrylate and 900g of a 95% by volume aqueous solution of ethanol was used. By this procedure was obtained a 49% by weight solution of a copolymer which solution had a viscosity of about 35,000 cps at 25°C.

The following examples illustrate formulations of cosmetic compositions of this invention.

EXAMPLE 8

A 2g quantity of each of the copolymer solutions obtained from Examples 1 to 7 were separately dissolved in 18g portions of ethanol. To each of the resulting solutions, 15g of trichloromonofluoromethane, 35g of dichlorodifluoromethane and 0.04g of a perfume were mixed and each mixture was charged into a glass pressure bottle fitted with a spray nozzle. By this procedure there was obtained a series of clear hair sprays.

Essentially the same procedure was used to prepare two other sprays which contained the conventional resins one of which was vinylether-maleic anhydride copolymer (X) and the other was polyvinyl pyrrolidone (Y) instead of a polymer formulation of this invention. Table 1 shows the various properties of the hair sprays prepared which were determined by the following test procedures.

A. Curl retention properties

Washed hair tresses (1g × 13cm) were curled on curlers, and then the curled hair was sprayed for 10 seconds by a spray from an aerosol spray nozzle held at a distance of 15 cm from the hair. The treated tresses were suspended in a humidity chamber at room temperature and a 95–100% relative humidity. The curl retention (C.R.) was calculated by the following equation:

$$\frac{L - L_t}{L - L_o} \times 100 = C.R. (\%)$$

wherein $L$ is the total length of the hair tress (13cm.), $L_o$ is the length after curling and setting, and $L_t$ is the length after 2 hours exposure in the humidity chamber.

B. Tackiness a. The hair tresses were treated and allowed to stand in the humidity chamber as described above (A). The tackiness of the tresses was tactually determined.

b. Films about 8 microns in thickness of the compositions were sprayed on glass plates which were left overnight in an air-conditioned chamber at 25°C. and at 40 and 65% R.H. Tackiness of the films was evaluated by a sward hardness rocker.

C. Flaking

The treated hair tresses described in (A) were dried at 60°C for 2 hours, and were suspended overnight in an air-conditioned chamber at 25°C and at 65% R.H. Flaking of the treated hair tresses was tested by running a comb through the tresses 50 times followed by visual observation.

D. Gloss

The glossiness of the treated hair tresses was tested by visual observation of the hair tresses which were treated by the procedure of (C).

TABLE I

| Resins Contained in Sprays | Curl Retention (%) | Tackiness | | Sward Rocker Hardness | | Flaking | Gloss |
| --- | --- | --- | --- | --- | --- | --- | --- |
| | | 65% R.H. | 95-100% R.H. | 40% R.H. | 65% R.H. | | |
| Example 1 | 95 | None | None | 58 | 46 | None | Good |
| Example 2 | 95 | None | None | 60 | 50 | None | Good |
| Example 3 | 96 | None | None | 60 | 48 | None | Good |
| Example 4 | 91 | None | None | 58 | 43 | None | Good |
| Example 5 | 93 | None | None | 60 | 44 | None | Good |
| Example 6 | 92 | None | None | 58 | 43 | None | Good |
| Example 7 | 93 | None | None | 60 | 44 | None | Good |
| X(conventional) | 80 | None | a little | 58 | 38 | None | Not Good |
| Y(conventional) | 50 | None | Much | 50 | 24 | Much | Not Good |

EXAMPLE 9

A 10g sample of each of the copolymer solutions obtained from Examples 1-7 was separately dissolved in 40g of ethanol. With each one of the resulting solutions was mixed 0.1g of perfume, 1g of a lanolin derivative and 49g of water. By this procedure was obtained a series of clear hair setting lotions.

EXAMPLE 10

A 1.5g sample of each of the copolymer solutions obtained from Examples 1-7 was separately dissolved in 20g of ethanol and 70g of water. With each one of the resulting solutions was mixed 0.5g of boric acid, 0.1g of perfume and 8g of polyethyleneglycol. By this procedure was obtained a series of acidic face lotions.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A sprayable hair-setting composition which comprises a hydrophilic copolymer and a solvent selected from the group consisting of water, a ($C_1$–$C_4$) aliphatic alcohol, dioxane, methylethyl ketone, acetone, tetrahydrofuran, ethylene glycol monomethyl ether, ethylene glycol monoethyl ether and mixtures thereof and a propellant, said hydrophilic copolymer having 3-95 per cent by weight of a structural unit of the formula

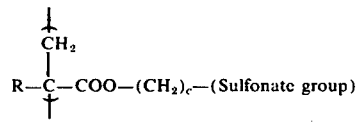

wherein R is H or methyl and c is an integer from 1 to 3 and 97 to 5% by weight of at least one comonomer selected from the group consisting of a ($C_1$–$C_{20}$) alkyl acrylate, a ($C_1$–$C_{20}$) alkyl methacrylate, a ($C_1$–$C_4$) hydroxyalkyl acrylate, and a ($C_1$–$C_4$) hydroxyalkyl methacrylate, said hydrophilic copolymer being present in an amount effective to set hair.

2. The sprayable hair-setting composition of claim 1 having 0.5 to 5 wt. % hydrophilic copolymer, 20-65 wt. % solvent and 30-79.5 wt. % propellant.

3. The sprayable hair-setting composition of claim 1, wherein the propellant is selected from the group consisting of a halogenated hydrocarbon gas and a liquefied petroleum gas.

* * * * *